(12) United States Patent
Chi et al.

(10) Patent No.: US 9,020,901 B2
(45) Date of Patent: Apr. 28, 2015

(54) BALANCING DATABASE WORKLOADS THROUGH MIGRATION

(71) Applicants: Yun Chi, Monte Sereno, CA (US); Vahit Hakan Hacigumus, San Jose, CA (US)

(72) Inventors: Yun Chi, Monte Sereno, CA (US); Vahit Hakan Hacigumus, San Jose, CA (US)

(73) Assignee: NEC Laboratories America, Inc., Princeton, NJ (US)

( * ) Notice: Subject to any disclaimer, the term of this patent is extended or adjusted under 35 U.S.C. 154(b) by 169 days.

(21) Appl. No.: 13/855,765

(22) Filed: Apr. 3, 2013

(65) Prior Publication Data

US 2013/0275382 A1 Oct. 17, 2013

Related U.S. Application Data

(60) Provisional application No. 61/620,151, filed on Apr. 4, 2012.

(51) Int. Cl.
*G06F 17/30* (2006.01)

(52) U.S. Cl.
CPC .................................. *G06F 17/303* (2013.01)

(58) Field of Classification Search
CPC .............................. G06F 17/303; G06F 9/505
USPC ............ 707/654, 602; 718/105; 709/208, 226
See application file for complete search history.

(56) References Cited

U.S. PATENT DOCUMENTS

| | | | |
|---|---|---|---|
| 7,376,743 B1 * | 5/2008 | Bazzinotti et al. | 709/229 |
| 2003/0018927 A1 * | 1/2003 | Gadir et al. | 714/4 |
| 2004/0071087 A1 * | 4/2004 | Siev et al. | 370/235 |
| 2005/0038834 A1 * | 2/2005 | Souder et al. | 707/203 |
| 2006/0167883 A1 * | 7/2006 | Boukobza | 707/10 |
| 2006/0200533 A1 * | 9/2006 | Holenstein et al. | 709/208 |
| 2008/0133687 A1 * | 6/2008 | Fok et al. | 709/207 |
| 2010/0023564 A1 * | 1/2010 | Yerneni et al. | 707/204 |
| 2011/0276649 A1 * | 11/2011 | Pujol et al. | 709/208 |
| 2011/0302277 A1 * | 12/2011 | Baker | 709/219 |
| 2012/0166492 A1 * | 6/2012 | Bikkula et al. | 707/803 |
| 2012/0254175 A1 * | 10/2012 | Horowitz et al. | 707/737 |
| 2012/0265741 A1 * | 10/2012 | Moon et al. | 707/694 |
| 2013/0262393 A1 * | 10/2013 | Mrak et al. | 707/659 |
| 2013/0306276 A1 * | 11/2013 | Duchesneau | 165/104.21 |
| 2014/0040343 A1 * | 2/2014 | Nickolov et al. | 709/201 |
| 2014/0108339 A1 * | 4/2014 | Marsden | 707/611 |
| 2014/0317315 A1 * | 10/2014 | Duchesneau | 709/250 |

* cited by examiner

*Primary Examiner* — Robert Beausoliel, Jr.
*Assistant Examiner* — Alexandria Bromell
(74) *Attorney, Agent, or Firm* — Joseph Kolodka

(57) ABSTRACT

A method for balancing database workloads among a plurality of database servers includes when a new server is available, selecting a set of master and slave databases to be migrated to the new server; and migrating the selected databases to result in a balanced new workload among all servers while minimizing migration cost; and during operation, if workload unbalance is detected in real time from a workload change in a certain database, iteratively selecting one database at a time to migrate to a different server to balance the workload.

18 Claims, 6 Drawing Sheets

BALANCING DATABASE WORKLOADS THROUGH MIGRATION

This application is a non-provisional application of U.S. Provisional Application Ser. No. 61/620,151 filed Apr. 4, 2012, the content of which is incorporated by reference.

BACKGROUND

The present invention relates to database workload balancing.

For various economic and business reasons enterprises are increasingly centralizing their backend computer systems in purpose built data centers. Data centers typically house high concentrations and densities of such computer systems and additionally provide databases to support customer needs. Data center operators have to make the decision to purchase the server boxes up-front and then provision resources on ever changing workload. Further, multiple different workloads may share resources on the same physical box and provisioning the workload requires taking into account physical constraints such as capacity constraints associated with the physical resources. The recent move towards cloud computing for data intensive computing presents unique opportunities and challenges for data center operators.

One key challenge that data center operators face is the provisioning of resources in the data center for specific customer workloads. For example, with a new server added, each existing server "donates" a set of masters and slaves to be migrated to the server so that
  there is no master-slave co-located on the new server,
  master-to-slave ratio are about the same across all the servers,
  memory capacities and CPU capacities are as balanced as possible across all the servers,
  amount of data being moved is minimal.

Another problem is hotspot elimination. For a given configuration of servers, if there are overloaded servers (a server is overloaded if it is a memory hotspot or a CPU hotspot, or both), resolve the overloading servers by migrating out one master from each overloaded server.

Federated databases have been used where relations are split manually among different servers and a unified view is exposed to the clients. However, such a solution involves manual configuration, special merging and wrapper algorithms, and does not support dynamic rebalancing.

Another solution is to add and remove slave databases based on workloads. However, because slave databases (replicas) only support read queries and all the write queries have to go to the master, such a solution can be ineffective when the workload contains many write queries. In addition, adding slaves takes very long time, and so this solution is not able to handle quick workload changes.

Other approaches have assumed that the workloads are different for a master DB and its slaves. Therefore, the workload is balanced through swapping the roles or master and slave. However, such method is only effective when the workloads at master and slaves are greatly different and the swapping is supported by the underlying DB system. In another method, the load balancing is achieved by (a) changing resource allocation among different virtual machines at the same server and (b) adding and removing servers. However, the method assumes each DB instance is wrapped within a single virtual machine and each server must contain all DBs (either all masters of all DBs, or one slave from each DB), thus limiting the applicability of the method.

SUMMARY

In one aspect, a method for balancing database workloads among a plurality of database servers includes when a new server is available, selecting a set of master and slave databases to be migrated to the new server; and migrating the selected databases to result in a balanced new workload among all servers while minimizing migration cost; and during operation, if workload unbalance is detected in real time from a workload change in a certain database, iteratively selecting one database at a time to migrate to a different server to balance the workload.

Advantages of the preferred embodiment may include one or more of the following. The system achieves workload balancing in databases by using database migration in real time. Such a solution has fast response time, involves minimum manual intervention, and can use different features (such as memory and CPU footprint) and metrics (such as workload variance, L1-norm of workload variation, master/slave ratio in a server, and so on) in the target function. The system achieves workload balancing among databases and so the overall system performance is optimized among all databases and all the servers. Faster operation is achieved. The system leverages techniques of live migration of memory-resident databases and so the operation is fast and the reaction to workload changes is quick. The system quickly finds a cost-effective database arrangement that minimizes the cost of running a workload. The system helps data center operators to provision for specific workloads while minimizing the total operating cost (TOC) of running the workload. Workload balancing can be achieve in real time through migration, and the ACID properties (atomicity, consistency, isolation, durability), which are required for most database systems, are guaranteed.

DETAILED DESCRIPTION

Figure 1:
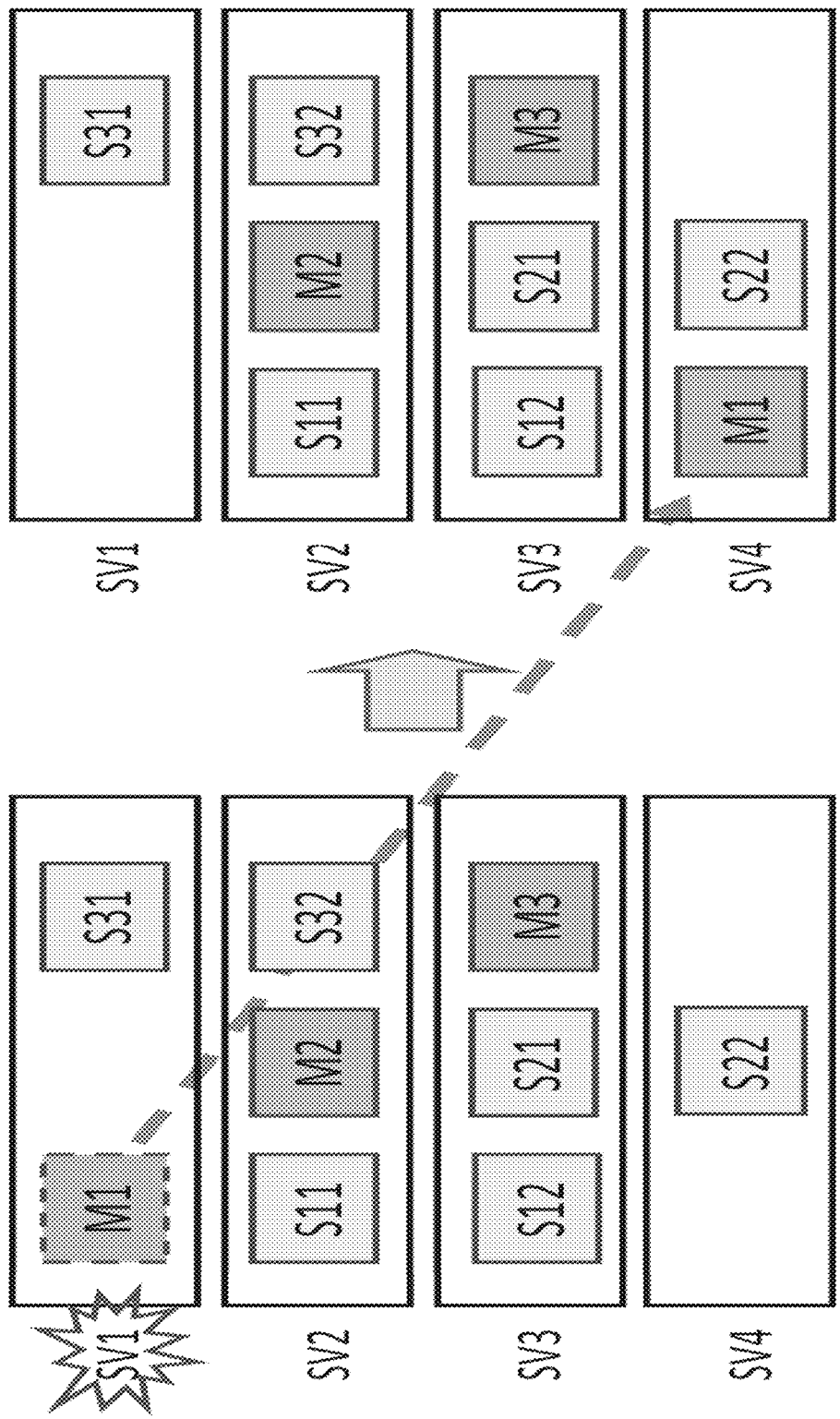
FIG. 1 illustrates an exemplary workload balancing achieved by migration database masters or slaves among servers

FIG. 1 illustrates an exemplary workload balancing achieved by migration database masters or slaves among servers. SV1-SV4 represent four servers, M1-M3 represent three database masters, and each database master has two corresponding database slaves (replicas). Thus, S11 and S12 are slaves of M1. First, when a new server is just started to handle more workload, the system selects a set of master and slave databases to be migrated to the new server. The selected databases to be migrated will result in the most balanced new workload among all servers (including the new server) while use the minimum amount of migration cost. In the new server, the master-to-slave ratio is similar to those in existing servers (i.e., the new server is as typical as any existing server after the migration is completed). Second, during operation, if workload unbalance is detected in real time, e.g., due to workload change in a certain database, our solution will iteratively select one database at a time to migrate to a different server, in order to balance the workload.

In one embodiment, M databases are hosted on N servers. Each database consists a primary DB (master) and ore or more secondary DBs (slaves), which are hosted on different servers. That is, a master DB cannot be co-located with any of its slaves on the same server, and neither can two slaves belonging to the same master be co-bated on the same server.

Each database has footprints on several system resources, such as CPU usage and memory usage, which can vary over time. Each server has a maximum resource capacity beyond which the server is considered overloaded. The resources are assumed to be additive, namely the server resource usage is the sum of resources usages of all the databases hosted on the server. Such an assumption is commonly accepted for CPU and memory usages. Preferably, the system performs live migration of DBs, e.g., the real-time migration capability from systems such as the NEC TAM. Next, terminologies are detailed:

The system consists of N servers, $SV_1, \ldots, SV_N$.

Server $SV_i$ contains $K_i$ tenants, $\{t_i^1, \ldots, t_i^{K_i}\}$. (Note: Different servers may have different numbers of tenants).

Each tenant $t_i^k$ is either a master or a slave. The master of a tenant cannot be co-located with any of its slaves on the same TAM server.

Each tenant $t_i^k$ has a footprint of memory usage $t_i^k$.mem and a footprint of CPU usage $t_i^k$.cpu The memory usage and CPU usage are additive in that for server $SV_i$, the total memory usage is $\Sigma_{k=1}^{K_i} t_i^k$.mem and the total CPU usage is $\Sigma_{k=1}^{K_i} t_i^k$.cpu The units of memory and CPU are interchangeable among servers (e.g., memory unit being Giga-Byte and CPU unit being Giga-cycles-per-second).

Each server $SV_i$ has a memory threshold $SV_i$.memTh and a CPU threshold $SV_i$.cpuTh that in normal conditions, should not go beyond. Once going beyond either memory or CPU threshold, we say the server becomes a hotspot (a memory hotspot or a CPU hotspot).

Each server $SV_i$ has a memory capacity $SV_i$.memCap (namely, extra memory capacity before $SV_i$ becomes a memory hotspot) and a CPU capacity $SV_i$.cpuCap. If $SV_i$.memCap<0 or $SV_i$.cpuCap<0, server $SV_i$ becomes a hotspot.

For each server $SV_i$.

$SV_i$.memCap: The memory capacity of server $SV_i$.

$SV_i$.cpuCap: The CPU capacity of server $SV_i$.

$SV_i$.memTh: The memory threshold of server $SV_i$, beyond which $SV_i$ becomes a memory hotspot.

$SV_i$.cpuTh: The CPU threshold of server $SV_i$, beyond which $SV_i$ becomes a CPU hotspot.

$SV_i$.tenants: The set of tenants $\{t_i^1, \ldots t_i^{K_i}\}$ that belong to server $SV_i$.

For each tenant $t_i^k$ such that $t_i^k \in SV_i$.tenants, $t_i^k$.tid: Tenant ID of $t_i^k$.

$t_i^k$.isMaster: A Boolean flag to indicate if $t_i^k$ is a master (or a slave).

$t_i^k$.mem: The memory usage of $t_i^k$.

$t_i^k$.cpu: The CPU usage of $t_i^k$.

$t_i^k$.dataSize: The size of data of $t_i^k$.

For N numbers $\{x_1, \ldots, x_N\}$, the mean $\mu_X$ and variance $\sigma_X^2$ are defined as $$\mu_X = \frac{1}{N}\sum_{i=1}^{N} x_i,$$

$$\sigma_X^2 = \frac{1}{N}\sum_{i=1}^{N}(x_i - \mu_X)^2.$$

With the above notation, a small variance implies balanced servers. If $\{x_1, \ldots, x_N\}$ represent the resource capacities (memory or CPU) among servers, then lower variance among $\{x_1, \ldots, x_N\}$ implies balanced servers. In another word, If $\Sigma_{i=1}^{N} x_i$ remains unchanged, then $\sigma_X^2$ is minimized when $x_1 = \ldots = x_N$. $\sigma_X^2$ is a good metric to measure the balance of resource capacity among servers.

Figure 2A:
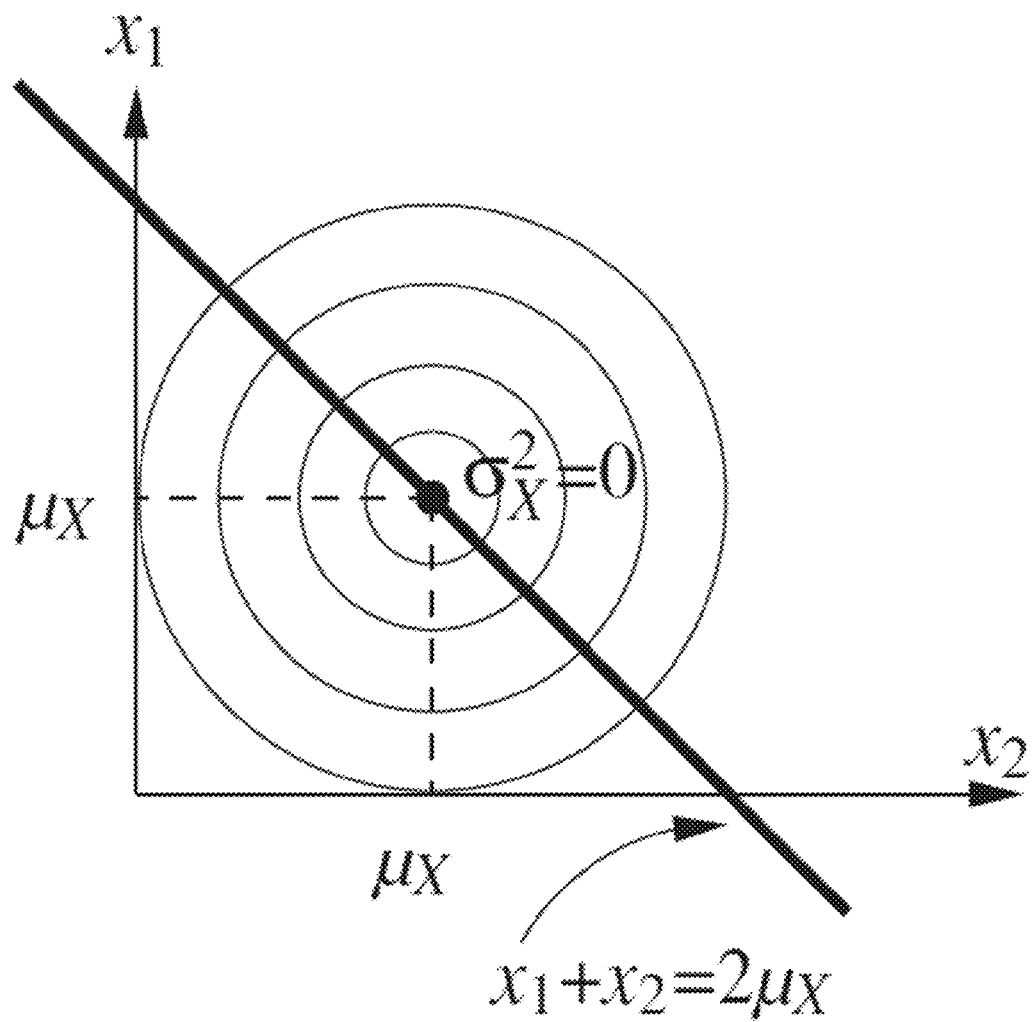
FIG. 2A illustrates a low variance implying balanced capacities, for N=2.
Figure 2B:
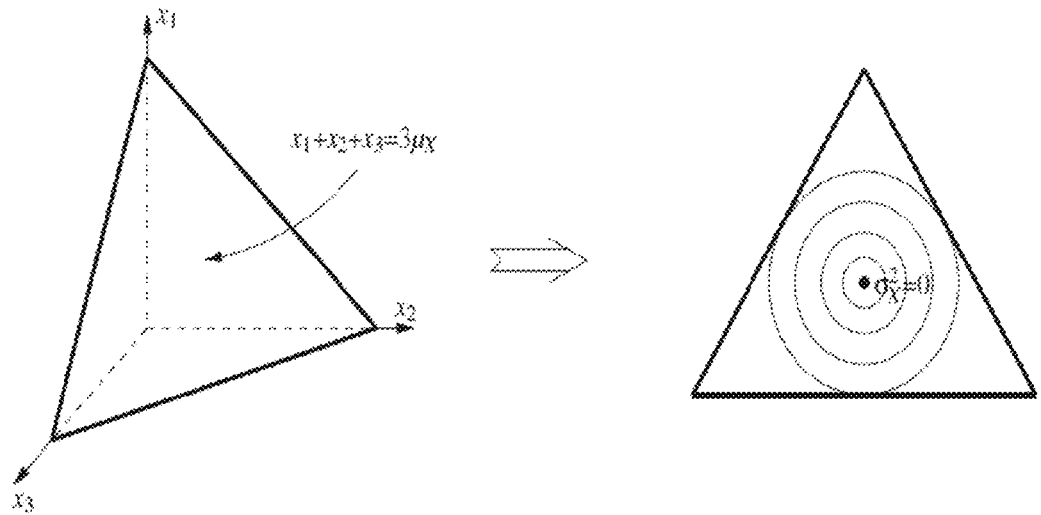
FIG. 2B is an exemplary illustration of low variance implying balanced capacities, for N=3.

FIG. 2A illustrates a low variance implying balanced capacities, for N=2. With $x_1 + x_2 = c$, where $c = 2\mu_X$ is a constant, the system simply redistributes values among $x_1$ and $x_2$. Since $x_1 + x_2 = 2\mu_X$, all the possible $\{x_1, x_2\}$ pairs are located on the line shown in the figure. In FIG. 1, the equi-lines with the same $\sigma_X^2$ values are shown (they turn out to be circles). As can be seen, when $x_1 = x_2 = \mu_X$, $\sigma_X^2$ achieves its minimal value 0; other than that, the more unbalanced the $\{x_1, x_2\}$ are, the higher the variance. This also works for N>2. FIG. 2B is an exemplary illustration of low variance implying balanced capacities, for N=3.

If $SV_i$ is a hotspot server with resource (for example, memory) capacity $x_i$ and $SV_j$ is a light-loaded server with resource capacity $x_j$. Then if the system migrates a tenant with resource usage $\Delta$ from $SV_j$ to $SV_i$, the reduction in variance for capacities among servers is $$f(\Delta) = \frac{2\Delta}{N}(x_i - x_j + \Delta).$$

If this variance reduction is treated as a function of $\Delta$, then $$\frac{\partial f(\Delta)}{\partial \Delta} = \frac{4\Delta}{N} + \frac{2}{N}(x_i - x_j) = 0,$$

from which the best tenant to migrate should have resource usage $\Delta^* = (x_j - x_i)/2$ and as a result of the migration, the change of variance is $-(x_j - x_i)^2/4$.

Figure 3:
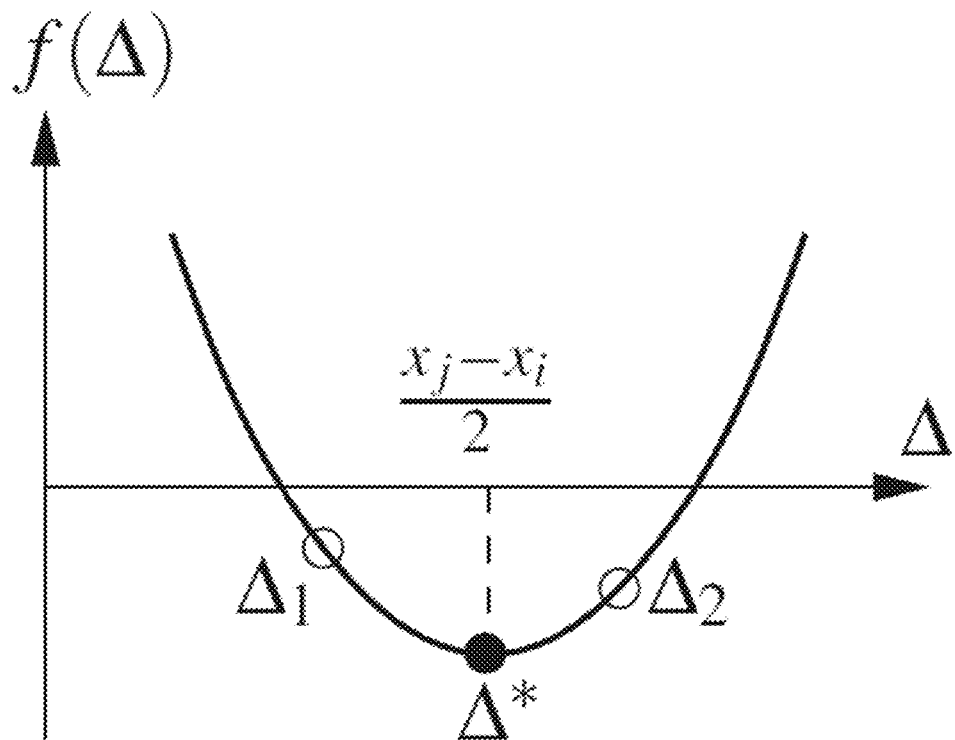
FIG. 3 shows an illustration that the optimal tenant may not exist.

The solution is to choose the largest resource capacity. The tenant resource usage are discrete values and it is not guaranteed that a tenant with resource usage of $\Delta^*$ can be found, as illustrated in FIG. 3, where the optimal $\Delta^*$ is not achievable, because the nearest tenant resource usages are $\Delta_1$ and $\Delta_2$. FIG. 3 shows this illustration that the optimal tenant may not exist.

Next, the process of new server migration is discussed. With a new server added, each existing server "donates" a set of masters and slaves to be migrated to the server so that there is no master-slave co-located on the new server, master-to-slave ratio are about the same across all the servers, memory capacities and CPU capacities are as balanced as possible across all the servers, amount of data being moved is minimal.

Pseudo-code for one exemplary Method 1 to migrate DBs to the new server is as follows:

```
input : SV1,...,SVN, the hotspot server SV1
output: tenant t migrate out and target server sv to migrate to
1   t ← null, sv ← null, change ← ∞;
2   for j ← 1 to N do
3   |   if (j ≠ i) then
4   |   |   gap ← xi − xj;
5   |   |   for k ← 1 to Ki do
6   |   |   |   c ← ti k,x · (gap + ti k,x);
7   |   |   |   if c < change then
8   |   |   |   |   change ← c;
9   |   |   |   |   sv ← SVj;
10  |   |   |   |   t ← ti k;
11  |   |   |   end
12  |   |   end
13  |   end
14  end
15  return t, sv;
```

A single resource X can be picked for illustration purpose, where X={$x_1, \ldots, x_x$} are the resource usages of the existing N servers {$SV_1, \ldots, SV_N$}. Now, a new server $SV_{N+1}$ is brought into the system. After each existing server donates some masters and slaves to the new server, assume the new resource usages in the N+1 servers are Y={$y_1, \ldots, y_N, y_{N+1}$}. Then the new mean and variance in resource usage are $$\lambda_Y = \frac{1}{N+1} \sum_{i=1}^{N+1} y_i,$$

$$\sigma_Y^2 = \frac{1}{N+1} \sum_{i=1}^{N+1} (y_i - \mu_Y)^2.$$

$$\mu_Y = \frac{N}{N+1} \mu_X$$

and is not affected by the exact configuration of tenants.

Method 1 can be used and invoked a number of times. The problem is different in that $SV_{N+1}$ was initially empty. So to fill up the empty $SV_{N+1}$ quickly, the greedy nature of Method 1 may favor migrating large tenants existing servers, and therefore may result in large-tenant-only on $SV_{N+1}$ and at the same time, leave large "holes" in the existing server capacities (i.e., some servers have large tenants migrated out while others have no tenants migrated out).

Based on the above consideration, Method 2 ignores the variance at the new server. That is, at each iteration, the method searches for a tenant t such that by migrating t into the new server $SV_{N+1}$, the variance reduction among the existing N servers (with respect to $\mu_Y$ instead of $\mu_X$) is maximized:

$$t = \underset{\text{server } i, \text{tenant } k}{\text{argmax}} \left\{ (y_i - \mu_Y)^2 - [(y_i - t_i^k) - \mu_Y]^2 \right\}.$$

```
input : {SV1,...,SVN,SVN+1}, bool reqMaster, int reqNum
output: updated system configuration {SV1,...,SVN,SVN+1}
1   (μmem,μcpu) ← (0,0), Q ← ∅;
2   for i ← 1 to N do
3   |   (μmem,μcpu) ← (μmem,μcpu) + (SV1.memCap,SV1.cpuCap);
4   end
5   (μmem,μcpu) ← (μmem,μcpu)/(N+1);
6   for i ← 1 to N do
7   |   (ti, δσi 2) ← SV1.pickBest(reqMaster,μmem,μcpu,SVN+1);
8   |   Q.insert((ti,δσi 2));
9   end
10  for k ← 1 to reqNum do
11  |   tj ← Q.top( );
12  |   Q.remove(tj);
13  |   SVN+1.add(tj);
14  |   SVj.remove(tj);
15  |   if (reqMaster) then
16  |   |   (tj, δσj 2) ← SVj.pickBest(reqMaster,μmem,μcpu,SVN+1);
17  |   |   Q.insert(tj);
18  |   else
19  |   |   Q.clear( );
20  |   |   for i ← 1 to N do
21  |   |   |   (ti, δσi 2) ← SVi.pickBest(reqMaster,μmem,μcpu);
22  |   |   |   Q.insert(ti,δσi 2));
23  |   |   end
24  |   end
25  end
26  return {SV1,...,SVN,SVN+1}
```

As shown above, Method 2 can be used for new server migration. In Method 2, among {$SV_1, \ldots, SV_N$}, there are |M| masters and |S| slaves. Then the method selects |M|/(N+1) masters and |S|/(N+1) slaves to migrate to the new server $SV_{N+1}$. To select |M|/(N+1) masters, Method 2 is called with parameters reqMaster=true and reqNum=|M|/(N+1); to select |S|(N+1) slaves, Method 2 is called with parameters reqMaster=false and reqNum=|S|/(N+1). Q is a priority queue, which sort the candidates by the variance reduction. In method 2:

Lines 2-5 compute the average resource usages $\mu_{mem}$ and $\mu_{mem}$ (with new server $SV_{N+1}$ included).

Lines 6-9 pick the best candidate tenant for migration for each server. Note that this candidate can be decided by each server locally, without consulting other servers.

Lines 11-14 move the best candidate among N servers to $SV_{N+1}$.

Lines 15-24 update the best candidate tenant of each server. If slaves are being migrated, the slave newly moved to $SV_{N+1}$ may invalidate the best candidate in other servers, and so re-computation is needed.

Next, the problem of hotspot elimination is discussed. For a given configuration of servers, if there are overloaded servers (a server $SV_i$ is overloaded if it is a memory hotspot with $SV_i$.memCap<0 or a CPU hotspot with $SV_i$.cpuCap<0, or both), resolve the overloading servers by migrating out one master from each overloaded server. This problem is illustrated in FIG. 1.

Figure 5:
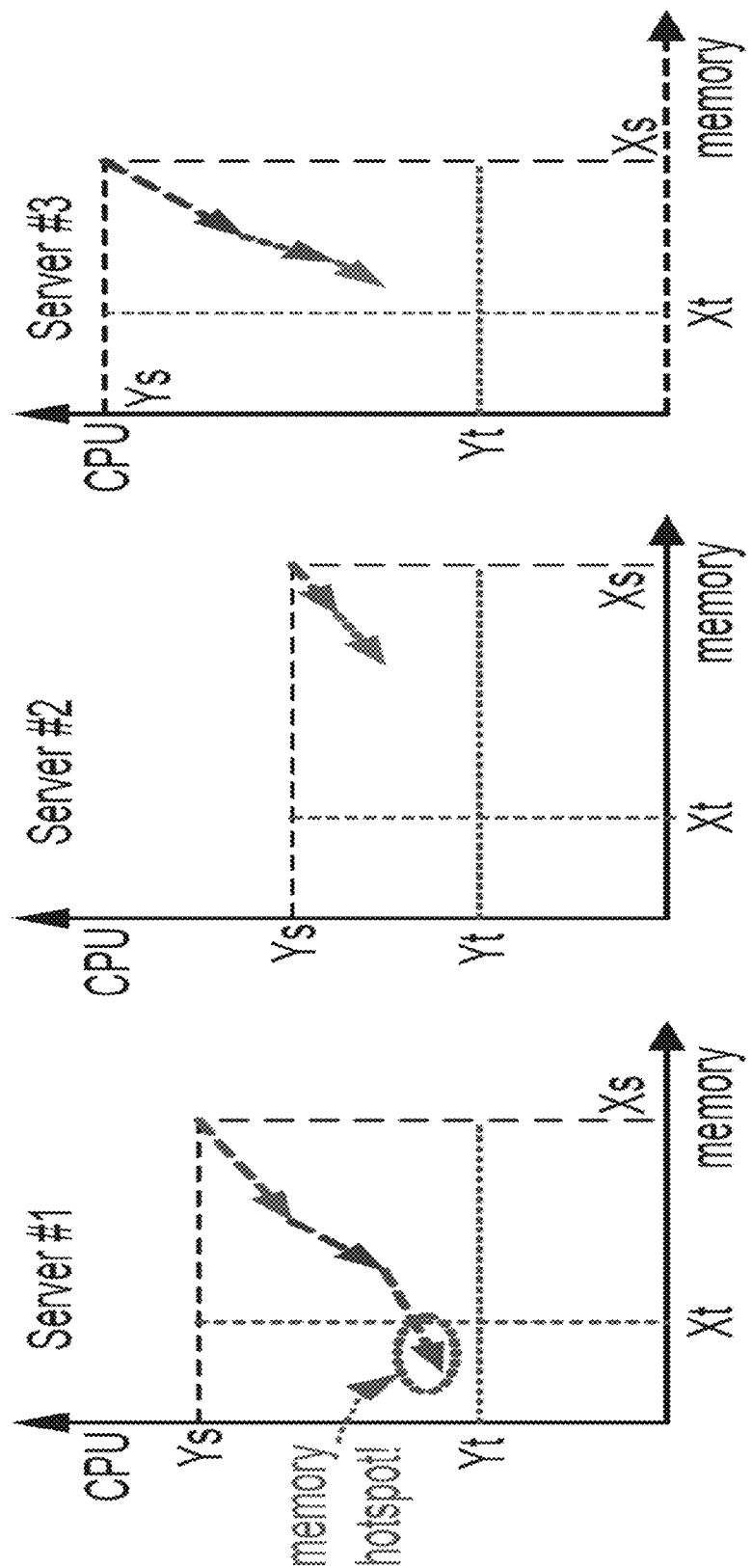
FIG. 5 is an illustration of a memory hotspot given multiple resources, namely memory and CPU.

There are two resources (memCap,cpuCap), instead of a single resource X. This will affect two things: (1) how hotspot is defined and (2) how the balance among servers is measured. For (1), a new server $SV_i$ a hotspot if either $SV_i$.memCap<0 or $SV_i$.cpuCap<0. In either case, the hotspot has to be eliminated. This is illustrated in FIG. 5 which is an illustration of a memory hotspot given multiple resources, namely memory and CPU.

For (2), a simple solution can be used by combining the variance of memory capacity and that of CPU capacity:

$$\sigma^2 = c_{mem} \cdot \sigma_{memCap}^2 + c_{cpu} \cdot \sigma_{cpuCap}^2,$$

where $c_{mem}$, and $c_{cpu}$ are parameters for calibrating the different units between memory and CPU (GB vs. G-cycle-per-sec).

In addition, $c_{mem}$ and $c_{cpu}$ can be used to control the emphasis on the balance of memory and that of CPU. For example, maybe CPU usage is more bursty and its balance is more important than that of memory usage, because the memory usage is relatively stable. A special case is to set $$c_{mem} = \frac{1}{\mu_{memCap}^2}$$

and $$c_{cpu} = \frac{1}{\mu_{cpuCap}^2}.$$

By doing this, the system essentially normalizes both $\mu_{memCap}$ and $\mu_{cpaCap}$ to 1 and treats the balance of memory and CPU as equally important. This consideration is reflected in lines 7, 8 and 11 of Method 3.

Because different tenants have different data sizes, the costs of migrating them are different. One solution is to revise the objective function as the ratio between the variance reduction of migrating t and the cost of migrating t. For example, if the migration cost for t is proportional to t's data size, the new metric is $$\frac{\sigma^2(t)}{t \cdot dataSize}$$

where $\sigma^2(t)$ is the variance reduction if t is migrated.

A master cannot co-located with any of its slaves. So a master at a hotspot server cannot be migrated to arbitrary servers. This has to be checked in the algorithm. That is, for a tenant t who is a candidate for migration, the system only considers target servers that do not have t's slaves on them.

The system considers candidate tenant and target server that eliminate the old hotspot and do not generate new hotspot. If such a solution does not exist, the algorithm returns null.

The input of the algorithm is $\{SV_1, \ldots, SV_N\}$. Among the servers, there might be more than one hotspots and so the solution of the algorithm should address all the hotspots. This makes the problem much more difficult. We choose to use a local greedy heuristic where the hotspots are eliminated one-by-one. That is, (1) each server hotspot is addressed by assuming it is the only hotspot, (2) the system configuration is hypothetically updated after each hotspot is addressed, (3) then the next hotspot is addressed by assuming the hypothetically updated system configuration, and (4) the algorithm declares failure if it cannot reach a final configuration where all hotspots are eliminated.

Note that this is heuristics because (1) we have to follow an order for which the hotspots are addressed and (2) for each hotspot we find a solution in a greedy manner where a less greedy solution may make next hotspot easier to eliminate.

Figure 4:
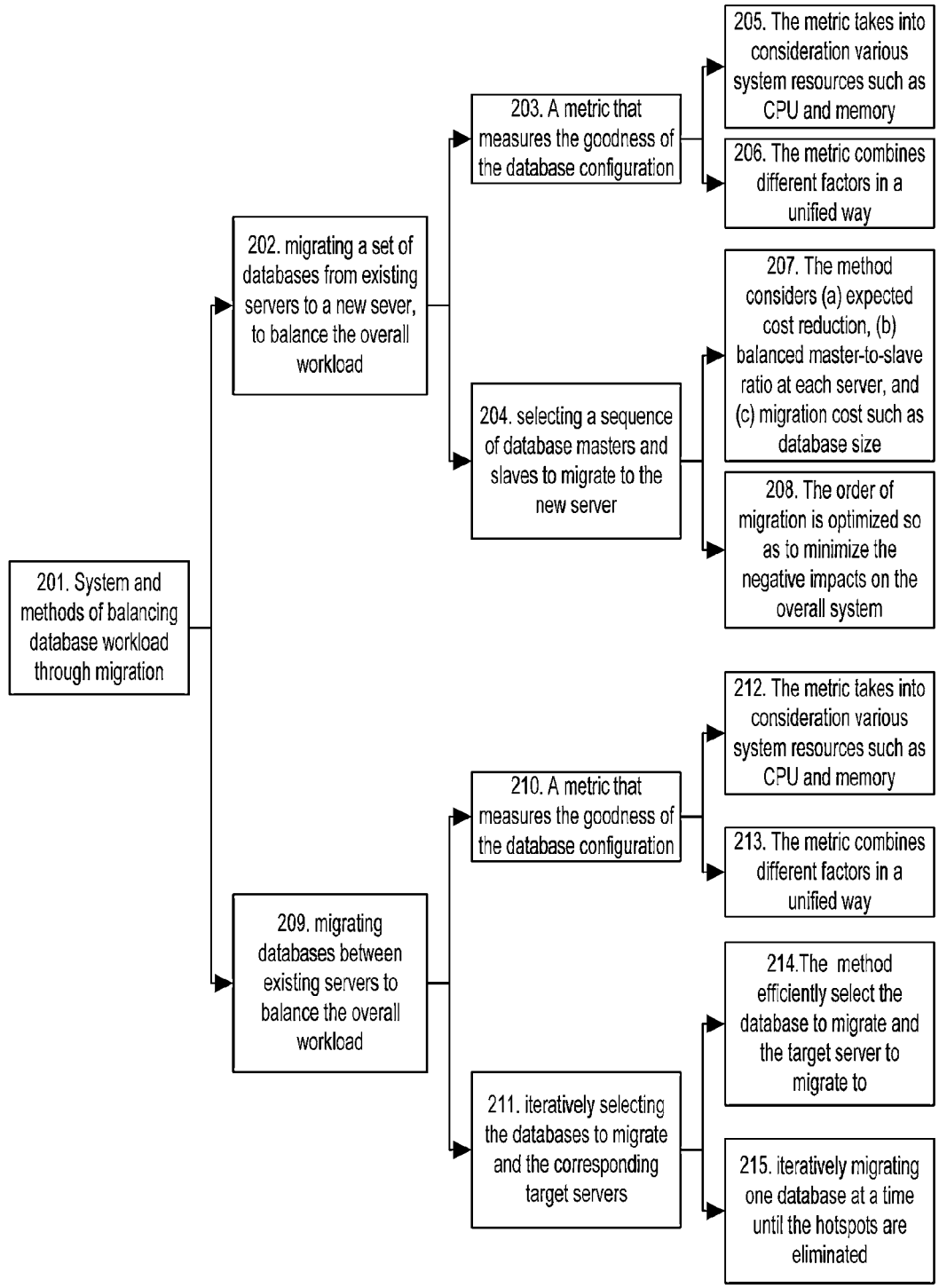
FIG. 4 is an illustration of the hotspot elimination problem.

FIG. 4 shows an exemplary process for balancing database workloads among several database servers by using database migration (201). The method includes migrating a set of databases from a set of existing servers to a newly available server so as to balance the workloads among servers (202) and a method of migrating databases among existing database servers so as to balance the workloads among the servers (209). The process uses a metric to measure the goodness of a given database configuration (203). The process also selects a sequence of database masters and slaves to migrate to the new server (204). In 205, the metric considers various system resources such as CPU usage and memory usage. In 206, the metric combines different factors in a unified way through a weighting strategy and a vector norm (Euclidean norm or L1 norm).

Turning now to 204, the method includes selecting a set of master databases and slave databases to be migrated to the newly available server. In 207, while making the selection, the method takes into consideration factors including (a) the expect cost reduction after the migration, (b) the master-to-slave ratio at each of the server after migration, and (c) the migration cost that is related to the size of each database. In 208, the method chooses an optimal order of migration so as to minimize the negative performance impact on the system during the process of migration.

The method includes migrating databases among existing database servers so as to balance the workloads among the servers (209). A metric can be used to measure the goodness of a given database configuration (210). In 212, the metric considers various system resources such as CPU usage and memory usage. In 213, the metric combines different factors in a unified way through a weighting strategy and a vector norm (Euclidean norm or L1 norm).

In an alternative, in 211, the method includes iteratively selecting the next database to migrate and the corresponding target database server, in order to eliminate all the hot spots. In 214, the method efficiently selects the next database to be migrated and the corresponding target server to be migrated to. In 215, the method iteratively migrates one database at a time until all the hot spots are eliminated.

```
   input : SV₁ the calling server, bool reqMaster, μ_mem, μ_cpu,
           SV_{N+1}
   output: t the tenant, δσ² variance reduction
1  t ← null, δσ² ← -∞;
2  foreach t_i^j ∈ SV₁ do
3  |  if (t_i^j.isMaster = reqMaster) and (t_i^j ∉ SV_{N+1}) then
4  |  |   Δ ← c_mem · (Σ_{k=1}^{K_i} t_i^k.mem - t_i^j.mem - μ_mem)² + c_cpu ·
   |  |     (Σ_{k=1}^{K_i} t_i^k.cpu - μ_cpu)²;
5  |  |   if Δ > δσ² then
6  |  |   |   t ← t_i^j;
7  |  |   |   δσ² ← Δ;
8  |  |   end
9  |  end
10 end
11 return (t, δσ²);
   input : SV1,...,SV_N, among which there could be hotspot
           servers
   output: strategy S = {(t,target)}: an ordered list of tenants to
           migrate and the corresponding target servers for
           migration
```

-continued

```
1   S ← ∅
2   for i ← 1 to N do
3   |   if SV_i.memCap < 0 or SV_i.cpuCap < 0 then
4   |   |   t ← null, sv ← null, change ← ∞;
5   |   |   for j ← 1 to N do
6   |   |   |   if (j ≠ i and SV_j.memCap > 0 and SV_j.cpuCap > 0)
    |   |   |   then
7   |   |   |   |   gap_mem ← SV_i.memCap − SV_j.memCap;
8   |   |   |   |   gap_cpu ← SV_i.cpuCap − SV_j.cpumCap;
9   |   |   |   |   for k ← 1 to K_i do
10  |   |   |   |   |   if (t_i^k.isMaster) and (t_i^k.tid ∉ SV_j) and
    |   |   |   |   |   (t_i^k.mem + SV_i.memCap > 0) and
    |   |   |   |   |   (t_i^k.cpu + SV_i.cpuCap > 0) then
    |   |   |   |   |   (−t_i^k.mem + SV_j.memCap > 0) and
    |   |   |   |   |   (−t_i^k.cpu + SV_j.cpuCap > 0) then
11  |   |   |   |   |   |   c ← [c_mem · t_i^k.mem · (gap_mem + t_i^k.mem) +
    |   |   |   |   |   |       c_cpu · t_i^k.cpu · (gap_cpu + t_i^k.cpu)]/ t_i^k.dataSize;
12  |   |   |   |   |   |   if c < change then
13  |   |   |   |   |   |   |   change ← c;
14  |   |   |   |   |   |   |   sv ← SV_j;
15  |   |   |   |   |   |   |   t ← t_i^k;
16  |   |   |   |   |   |   end
17  |   |   |   |   |   end
18  |   |   |   |   end
19  |   |   |   end
20  |   |   end
21  |   |   if t = null then
22  |   |   |   return failure;
23  |   |   else
24  |   |   |   S.append((t,sv));
25  |   |   |   SV_i.tenants.remove(t);
26  |   |   |   SV_sv.tenants.insert(t);
27  |   |   |   SV_i.memCap ← SV_i.memCap + t.mem;
28  |   |   |   SV_i.cpuCap ← SV_i.cpuCap + t.cpu;
29  |   |   |   SV_sv.memCap ← SV_i.memCap + t.mem;
30  |   |   |   SV_sv.cpuCap ← SV_i.cpuCap + t.cpu;
31  |   |   end
32  |   end
33  end
34  return S;
```

Figure 6:
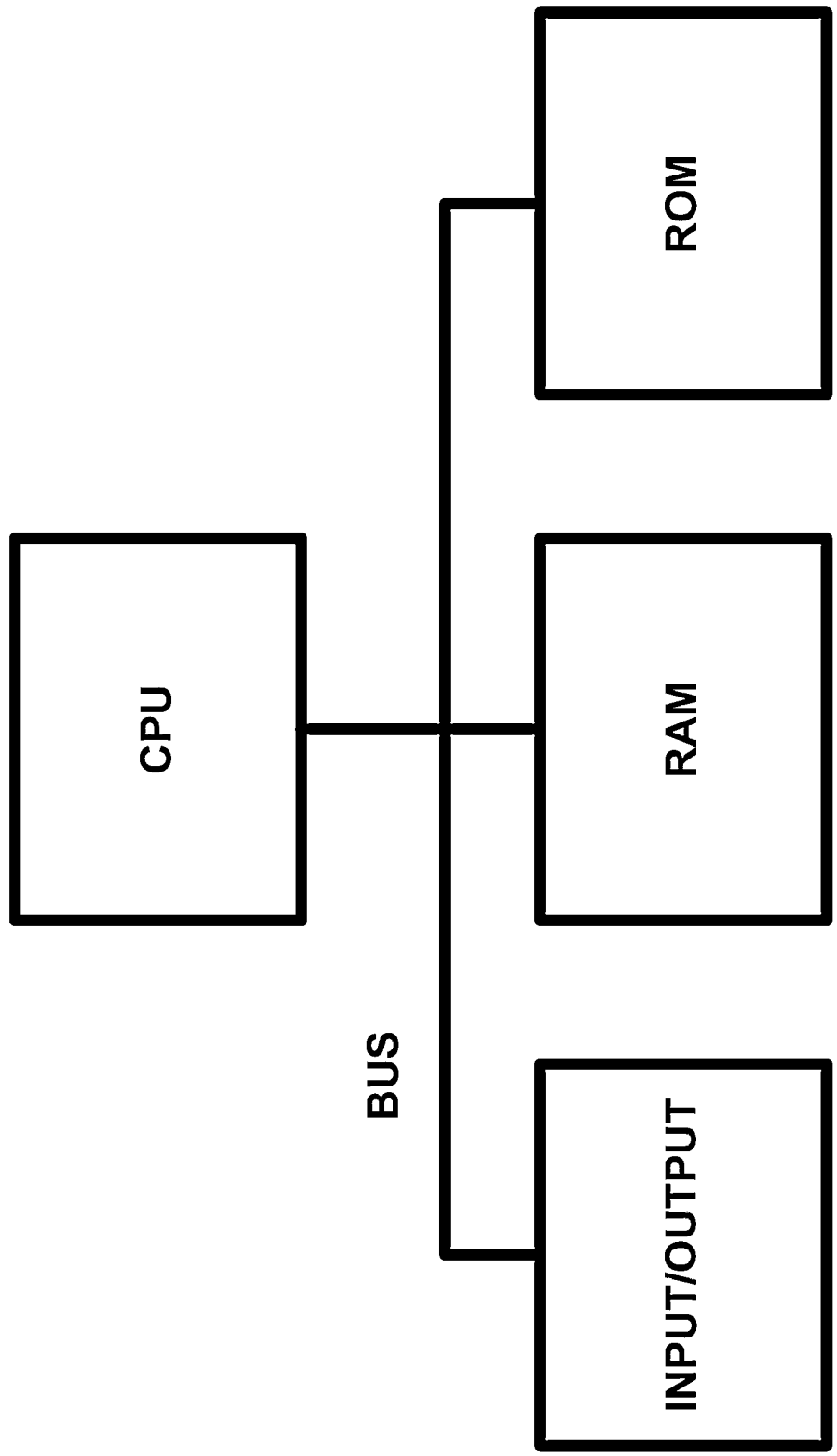
FIG. 6 shows an exemplary computer to perform database balancing.

FIG. 6 shows an exemplary computer to perform database balancing. The system may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

By way of example, a block diagram of a computer to support the system is discussed next in FIG. 6. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

The system has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for balancing database workloads among a plurality of database servers, the method comprising:
    when a new server is available, selecting a set of master and slave databases to be migrated to the new server and migrating the selected databases to result in a balanced new workload among all servers while minimizing migration cost;

during operation, if a workload unbalance is detected in real-time from a workload change, iteratively selecting one database at a time to migrate to a different server to balance the workload; and determining a metric for a given database configuration including a mean and a variance, wherein the variance is determined as:

$$\sigma^2 = c_{mem} \cdot \sigma_{memCap}^2 + c_{cpu} \cdot \sigma_{cpuCap}^2,$$

where $c_{mem}$ and $c_{cpu}$ are parameters for calibrating different units between memory and a CPU.

2. The method of claim 1, comprising applying a metric to measure a goodness of a given database configuration.

3. The method of claim 2, wherein the metric comprises system resources including processor (CPU) usage and memory usage.

4. The method of claim 2, wherein the metric comprises different factors in a unified way through a weighting strategy and a vector norm.

5. The method of claim 1, wherein the selecting a set of master databases and slave databases for migration further comprises considering one or more factors including (a) the expect cost reduction after the migration, (b) the master-to-slave ratio at each of the server after migration, and (c) the migration cost that is related to the size of each database.

6. The method of claim 1, comprising choosing an optimal order of migration to minimize impact on the system during migration.

7. The method of claim 1, comprising iteratively selecting a next database to migrate and a corresponding target database server to eliminate a hot spot.

8. The method of claim 1, comprising iteratively migrating one database at a time until all hot spots are eliminated.

9. The method of claim 1, comprising setting $$c_{mem} = \frac{1}{\mu_{memCap}^2} \text{ and } c_{cpu} = \frac{1}{\mu_{cpuCap}^2}.$$

10. A system for balancing database workloads among a plurality of database servers, the system comprising:
a processor;
code executable by the processor when a new server is available, including instructions for selecting a set of master and slave databases to be migrated to the new server; and migrating the selected databases to result in a balanced new workload among all servers while minimizing migration cost; and code executable by the processor during operation, including instructions for detecting if workload unbalance is detected in real time and iteratively selecting one database at a time to migrate to a different server to balance the workload; and code for determining a metric for a given database configuration including a mean and a variance, wherein the variance is determined as:

$$\sigma^2 = c_{mem} \cdot \sigma_{memCap}^2 + c_{cpu} \cdot \sigma_{cpuCap}^2,$$

where $c_{mem}$ and $c_{cpu}$ are parameters for calibrating different units between memory and a CPU.

11. The system of claim 10, comprising code for applying a metric to measure a goodness of a given database configuration.

12. The system of claim 11, wherein the metric comprises system resources including processor (CPU) usage and memory usage.

13. The system of claim 10, wherein the metric combines different factors in a unified way through a weighting strategy and a vector norm.

14. The system of claim 10, wherein the code for selecting a set of master databases and slave databases for migration further comprises considering one or more factors including (a) the expect cost reduction after the migration, (b) the master-to-slave ratio at each of the server after migration, and (c) the migration cost that is related to the size of each database.

15. The system of claim 10, comprising code for choosing an optimal order of migration to minimize impact on the system during migration.

16. The system of claim 10, comprising code for iteratively selecting a next database to migrate and a corresponding target database server to eliminate a hot spot.

17. The system of claim 10, comprising code for iteratively migrating one database at a time until all hot spots are eliminated.

18. The system of claim 10, comprising code for setting $$c_{mem} = \frac{1}{\mu_{memCap}^2} \text{ and } c_{cpu} = \frac{1}{\mu_{cpuCap}^2}.$$

* * * * *